United States Patent
Levels et al.

(10) Patent No.: US 10,132,787 B2
(45) Date of Patent: Nov. 20, 2018

(54) DEVICE FOR OPTICALLY DETERMINING THE CONCENTRATION OF ALCOHOL AND CARBOHYDRATES IN A LIQUID SAMPLE

(71) Applicant: Haffmans B.V., Venlo (NL)

(72) Inventors: Geert Hubert Willem Levels, Venlo (NL); Emile Thomas Martinus Johannes Martynowicz, Venlo (NL)

(73) Assignee: Haffmans B.V., Venlo (NL)

(*) Notice: Subject to any disclaimer, the term of this patent is extended or adjusted under 35 U.S.C. 154(b) by 0 days.

(21) Appl. No.: 14/476,990

(22) Filed: Sep. 4, 2014

(65) Prior Publication Data

US 2015/0060674 A1    Mar. 5, 2015

(30) Foreign Application Priority Data

Sep. 5, 2013  (NL) .................................... 2011388

(51) Int. Cl.
*G01J 5/02*      (2006.01)
*G01N 33/14*     (2006.01)
*G01N 21/3577*   (2014.01)
*G01N 21/21*     (2006.01)
*G01N 21/31*     (2006.01)
*G01N 21/359*    (2014.01)
(Continued)

(52) U.S. Cl.
CPC ............. *G01N 33/14* (2013.01); *G01N 21/21* (2013.01); *G01N 21/3151* (2013.01);
(Continued)

(58) Field of Classification Search
USPC .............. 250/339.07, 339.08, 339.12, 343; 356/322
See application file for complete search history.

(56) References Cited

U.S. PATENT DOCUMENTS 3,724,952 A  4/1973  Vossberg
5,239,180 A  8/1993  Clarke
(Continued)

FOREIGN PATENT DOCUMENTS

DE       4138419 A1       5/1993
EP       1965193 A1       9/2008
WO    20040044558 A2      5/2004

OTHER PUBLICATIONS

Veale et al. "An On-Line Approach to Monitor Ethanol Fermentation Using FTIR Spectroscopy" Biotechnol. Prog. 2007, 23, p. 494-500.*

(Continued)

*Primary Examiner* — David Porta
*Assistant Examiner* — Mamadou Faye
(74) *Attorney, Agent, or Firm* — Quarles & Brady LLP

(57) ABSTRACT

Disclosed is a device for optically determining a concentration of alcohol and carbohydrates in a liquid sample. The device includes at least a first and a second light source arranged for exposing the liquid sample in a wavelength range between 750 nm and 1000 nm, a spectrometer arranged to determine a first and a second light intensity by measuring the light from the first and the second light source, a processing unit which is connected to the spectrometer and which is arranged to determine an absorption value of the liquid sample from a comparison of the first and the second light intensity with a reference value. In certain aspects, the device may further include a processing unit that calculates concentrations of alcohol and/or carbohydrates and at least two polarization filters.

13 Claims, 1 Drawing Sheet

(51) Int. Cl.
*G01N 21/03* (2006.01)
*G01N 21/85* (2006.01)
*G01J 3/427* (2006.01)

(52) U.S. Cl.
CPC ....... *G01N 21/359* (2013.01); *G01N 21/3577* (2013.01); *G01N 33/146* (2013.01); *G01J 2003/4275* (2013.01); *G01N 21/031* (2013.01); *G01N 21/0332* (2013.01); *G01N 21/85* (2013.01); *G01N 2201/0624* (2013.01)

(56) References Cited

U.S. PATENT DOCUMENTS

| | | | | |
|---|---|---|---|---|
| 5,679,955 A | * | 10/1997 | Schmidt et al. | 250/343 |
| 5,920,393 A | * | 7/1999 | Kaplan | 356/364 |
| 6,119,026 A | * | 9/2000 | McNulty et al. | 600/310 |
| 6,700,661 B1 | * | 3/2004 | Cadell | G01J 3/28 250/252.1 |
| 7,532,325 B2 | * | 5/2009 | Ahmed et al. | 356/327 |
| 8,106,361 B2 | * | 1/2012 | Benes | 250/339.12 |
| 2004/0240712 A1 | * | 12/2004 | Rowe et al. | 382/124 |
| 2008/0282779 A1 | | 11/2008 | Noguchi et al. | |
| 2009/0201491 A1 | * | 8/2009 | Busch | G01J 3/02 356/51 |
| 2009/0270701 A1 | * | 10/2009 | Osaki et al. | 600/316 |

OTHER PUBLICATIONS

European Search Report and Written Opinion for NL Patent Application 2011388 dated Apr. 8, 2014.

\* cited by examiner

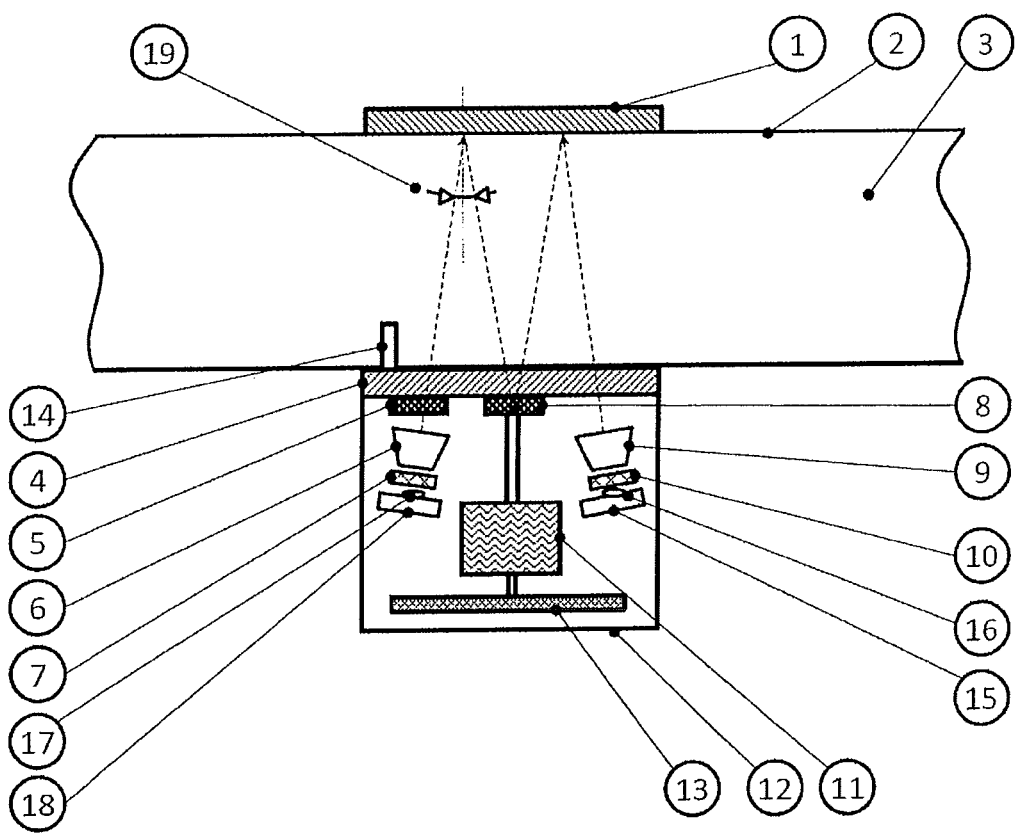

DEVICE FOR OPTICALLY DETERMINING THE CONCENTRATION OF ALCOHOL AND CARBOHYDRATES IN A LIQUID SAMPLE

CROSS REFERENCE TO RELATED APPLICATION

This application claims priority from NL Patent Application No. 2011388 filed on Sep. 5, 2013, the entirety of which are incorporated herein by reference.

TECHNICAL FIELD AND BACKGROUND OF THE INVENTION

The invention relates to a device and a method for optically determining a concentration of alcohol and carbohydrates in a liquid sample.

It is known to use optical measuring devices to determine properties such as alcohol (e.g., ethanol) concentrations in consumptive liquids, including, for example, beer, wine, liquor, soft drinks, and low-alcohol or non-alcoholic beer. It is also usually desirable to determine the concentration of other components in the consumptive liquid besides alcohol. In particular, it may be desirable to further determine the concentration of carbohydrates in beer, wine, liquors or the other above mentioned beverages. Said carbohydrates, also called sugars or saccharides, are a specific type of compounds having carbon, hydrogen and oxygen atoms, in which hydrogen and oxygen atoms are present in a 2:1 proportion, the general formula being $C_n(H_2O)_m$. The carbohydrate family or sugars also includes monosaccharides, disaccharides, and polysaccharides, among other substances. Examples may include glucose ($C_6H_{12}O_6$), maltose ($C_{12}H_{22}O_{11}$), dextrine $(C_8H_{10}O_5)_n$, fructose, sucrose, etc. In those cases in which carbohydrates or sugars are mentioned herein, reference is made to the above definition.

EP 1 965 193 A1 discloses a device suitable for determining a concentration of alcohol in which a spectrometer is used to determine light absorption at specific wavelengths. Based on light absorption, the concentration of alcohol in the sample can subsequently be determined.

For example, a liquid sample is exposed by means of a light source and the received light intensity is determined by means of a sensor. Because different components of the liquids exhibit different levels of absorption at different wavelengths, it is possible to determine the concentration of the components in the liquids on the basis of the absorbed light intensity.

The aforesaid device comprises a light source and a sensor, which are arranged to measure the light intensity having at least two wavelengths. Since the light absorption of water and alcohol, and in particular ethanol, hardly differ from each other at the first wavelength, whereas they do differ from each other at the second wavelength, it is possible to determine the concentration of alcohol from the proportion on the basis of said difference. The drawback, however, is the fact that one sensor is used, which must be arranged to capture light at two wavelengths. Thus there can be no question of simultaneous measurements at the different wavelengths. Accordingly, reference is explicitly made to measurements being carried out in succession at the different wavelengths.

BRIEF SUMMARY OF THE INVENTION

To potentially obviate the above discussed problem, more than one sensor may be used. However, when using more than one sensor, light must somehow be separated to measure light/absorption at a first and a second wavelength. Usually, such measuring devices are therefore provided with a monochromator or similar complex diffraction elements.

Accordingly, it is an object of the invention to provide a device in which the amount of alcohol and the amount of sugars in a liquid can be measured in a precise and simple manner.

This object is achieved by providing, in a first embodiment, a device for optically determining a concentration of alcohol and carbohydrates in a liquid sample. In certain aspects, this device includes:

at least a first and a second light source arranged for exposing the liquid sample in a wavelength range between 750 nm and 1000 nm;

a spectrometer arranged to determine a first and a second light intensity by measuring the light from the first and the second light source;

a processing unit which is connected to the spectrometer and which is arranged to determine an absorption value of the liquid sample from a comparison of the first and the second light intensity with a reference value. In certain aspects, the processing unit is further arranged to calculate the concentration of alcohol from the proportion of the absorption at a wavelength of less than 900 nm and the wavelength range between 900 nm and 920 nm, and to calculate the concentration of carbohydrates alcohol from the proportion of the absorption in the wavelength range between 750 nm and 900 nm and at a wavelength of 900 nm. In this aspect, the device further includes at least two polarization filters for filtering the light from the first light source, wherein the first polarization filter is disposed between the first light source and the liquid sample and the second polarization is disposed between the liquid sample and the spectrometer.

The disclosed device is suitable for determining the received light intensity emitted through the liquid sample by the first and the second light source. Subsequently, the absorption of the light can be determined on the basis of the received intensity, which absorption is inversely proportional thereto. Surprisingly it has been found that the concentration of alcohol can be derived with a high degree of accuracy from the proportion between the absorption at a wavelength of less than 900 nanometer (nm), and the wavelength in the range between 900 nm and 920 nm. Accordingly, it is possible to derive with a high degree of accuracy the concentration of carbohydrates in the liquid sample from the proportion between the absorption at a wavelength of more than 900 nm and the wavelength range between 750 nm and 900 nm.

From the prior art it is known to determine the concentration of alcohol by means of two wavelengths, using light beams, for example. However, such a device must be provided with a monochromator or other diffraction element in order to be able to distinguish between the light beams or light sources. The device according to a first embodiment to that end includes polarization filters disposed in the path of one of the light beams, however. The light beams can be filtered by means of said polarization filters and be distinguished from each other. Thus, a device according to such an embodiment is not only capable of accurately determining the concentrations of alcohol and carbohydrates, but achieves this result in a simple and compact manner.

In certain aspects, the device is arranged to determine concentrations of alcohol and carbohydrates. Within this framework the term "alcohol" is understood to include various types of alcohol, such as in particular ethanol, present in consumer liquids. Similarly, the term "carbohydrates" is understood to refer to those carbohydrates that can occur in such liquids under the family name of carbohydrates, also called sugars or saccharides. In particular they may include one or more of glucose ($C_6H_{12}O_6$), maltose ($C_{12}H_{22}O_{11}$), dextrine ($C_6H_{10}O_5$)$_n$, fructose, sucrose, etc. More in general, the measuring device is arranged to determine concentrations of alcohol, such as ethanol, in combination with extract(s) having carbohydrates such as glucose, maltose, dextrine, fructose, sucrose etc. However, in the case of non-alcoholic beer or soft drinks, for example, it may suffice to measure only the carbohydrate concentration or to determine that the alcohol concentration is zero.

In a specific embodiment of the device for optically determining a concentration of alcohol and carbohydrates in a liquid sample, the first and the second polarization filter are positioned at an angle relative to each other such that angle ranges between 10 and 170 degrees, in particular between 30 and 150 degrees, more particular between 30 and 130 degrees.

According to one embodiment, the two light sources may be aligned at an angle of less than 180 degrees relative to each other. The light that is emitted by the light sources can thus be directed at a reflecting surface that is disposed opposite the chamber for the liquid sample. The light reflected from there is directed at the entrance aperture of the spectrometer. The closer the light sources are disposed to the spectrometer, the greater the aforesaid angle will be. In an advantageous embodiment, said angle ranges from 10 to 170 degrees, 20 to 160 degrees, 30 to 150 degrees, 40 to 140 degrees, 50 to 130 degrees, 60 to 120 degrees, 70 to 110 degrees, 80 to 100 degrees or amounts to about 90 degrees. In a configuration in which the light sources are disposed on the side of the liquid chamber for the liquid sample opposite the spectrometer, the angle will be smaller, because the light is in that case focused directly to the entrance aperture of the spectrometer without being reflected.

In another embodiment of the device for optically determining the concentration of alcohol and carbohydrates in a liquid sample, the processing unit is arranged to formulate a linear equation from a multitude of reference measurements and to calculate the concentrations of carbohydrates and alcohol from said linear equation.

In one example, the processing unit, also called arithmetic unit, or more in general electronics, may be arranged to carry out one or preferably several reference measurements prior to measuring the liquid sample. Said measurements are carried out by measuring a water spectrum (reference) at various temperatures (D) and measuring a product spectrum (adsorption) and temperature of a known, laboratory-determined alcohol concentration. The absorption spectrum is then determined from the proportion of the product spectrum and the water spectrum, according to the formula $$-{}^{10}\log(\text{product spectrum}(T)/\text{water spectrum}(T))$$

Subsequently, the absorption value is determined by means of an arithmetic model within a particular wavelength range, which absorption value is linked to the known alcohol value as previously determined on the known product spectrums. Said previous steps are repeated for a multitude of or call concentrations, from which subsequently an equation is formulated (by means of interpolation). The absorption value, which is obtained by measurements carried out on the liquid sample, is input in said (linear) equation for determining concentrations of alcohol and carbohydrates (sugars) therefrom.

In one embodiment, the device, and in particular the processing unit, may be arranged to carry out a background spectrum measurement prior to the aforesaid steps. This takes place in the dark, with the light sources turned off. Subsequently, the electronic noise in the spectrum is measured in a next step. Following this, the previously described steps of the various water and reference product spectrum measurements are carried out.

In another embodiment of the device for optically determining a concentration of alcohol and carbohydrates in a liquid sample, the device further includes a reflecting surface for reflecting the light from the first and the second light source to the spectrometer.

The use of a reflecting surface disposed opposite the measuring chamber or, in other words, the liquid chamber, in which the liquid sample is present, has the advantage that the light sources and the light sensor, or the spectrometer, can be accommodated in one and the same housing. This has a positive effect as regards the size and the complexity of the device.

In another embodiment of the device for optically determining a concentration of alcohol and carbohydrates in a liquid sample, the device further comprises a first and a second lens element for focusing the light from the first and the second light source to the spectrometer.

Since the light from the light sources need not directly provide a pointed light source, a lens element may be provided. Non-pointed or parallel light beams, such as diffuse light beams, can be focused to the entrance aperture of the spectrometer via the reflecting surface by means of said lens element.

In a next embodiment of the device for optically measuring the concentration of alcohol and carbohydrates in a liquid sample, the device further includes a window for closing the device to the liquid sample, wherein the window may be arranged, for example, to only transmit light in the wavelength range between 750 nm and 1000 nm.

In order to ensure that the light provided by the light sources outside the measuring chamber can indeed reach said measuring chamber, the measuring device is closed by a light-transmitting window. Said window separates the device from the measuring chamber. Since the operative light is light in the wavelength range between 750 nm and 1000 nm, the light sources of one embodiment may be arranged to provide light in said wavelength range or, in an alternative embodiment, the window can act as a filter for blocking light outside said range.

In an alternative embodiment of the device for optically determining a concentration of alcohol and carbohydrates in a liquid sample, the device further includes a temperature sensor for determining the temperature of the liquid sample.

To guarantee constant, reliable measuring values, one embodiment of the device is provided with a temperature sensor for determining the temperature of the liquid sample. If the measured temperature falls outside a particular range, the device can indicate this, making it possible to determine the reliability of the concentrations being generated at that point. In another embodiment, the device may be provided with a temperature sensor for measuring the temperature of the light source. As the light from many light sources, such as LEDs, depends on the temperature, it is desirable to be able to determine the temperature.

The device is in principle arranged to be operational at a specific temperature of the light source. To contribute to the accuracy of the device, it is possible to determine, using a temperature sensor, whether the desired temperature is indeed reached. In another embodiment, the light source may be provided with a temperature measuring device, such as a Peltier element, so as to safeguard the temperature.

In another embodiment of the device for optically determining a concentration of alcohol and carbohydrates in a liquid sample, the device further includes temperature control means for maintaining the liquid sample at a constant, predetermined temperature.

Since the measuring set-up may be calibrated for a specific temperature of the liquid sample, the sample can be heated or cooled in one embodiment when the sensor detects that the sample does not have the correct temperature for ensuring a reliable measurement.

In a next embodiment of the device for optically determining a concentration of alcohol and carbohydrates in a liquid sample, at least one of the first light source the second light source and the spectrometer comprises a monochromator.

Using a monochromator, light having different wavelengths can be filtered so as to make it possible to measure the absorption or the light intensity of a part thereof by only transmitting light of a particular wavelength.

In a specific embodiment of the device for optically determining a concentration of alcohol and carbohydrates in a liquid sample, the liquid sample is a sample of one of the liquids from the group consisting of: beer, wine, liquors, and non-alcoholic beverages, non-alcoholic beer and soft drinks.

Examples of liquids for which the measuring device is suitable include, but are not limited to, beer, wine and (distilled) liquors, but the device is also capable of determining the concentration of alcohol and carbohydrates of other alcoholic beverages. Examples thereof are low-alcohol beer and non-alcoholic beer. In each embodiment, the device is arranged to measure concentrations of alcohol in non-alcoholic beverages, such as soft drinks and non-alcoholic beer. The device is arranged to measure concentrations of alcohol; in some cases, however, there is no need to know this value, for example in the case of soft drinks. In the case of non-alcoholic beer it may be desirable, for example for reasons of religious conviction, to determine that the concentration of alcohol is zero. Consequently, the device, in all embodiments thereof, is arranged to determine the concentrations of carbohydrates and alcohol, but in a practical embodiment it is also suitable for determining only the concentration of carbohydrates or for determining (in combination therewith) that a particular sample does not contain any alcohol.

In a second embodiment, there is provided a method for optically determining a concentration of alcohol and carbohydrates in a liquid sample, including the steps of:

exposing the liquid sample by means of at least a first and a second light source, which light sources are arranged to alternately expose the liquid sample in a wavelength range between 750 nm and 1000 nm;

determining a first and a second light intensity by means of a spectrometer by measuring the light from the first and the second light sources;

determining, by means of a processing unit, an absorption value of the liquid sample from a comparison of the first and the second light intensity with a reference value; and calculating, by means of the processing unit, the concentration of alcohol from the proportion of the absorption in the wavelength range of less than the 900 nm and the wavelength range between 900 nm and 920 nm and the concentration of carbohydrates from the proportion of the absorption between 750 nm and 900 nm and the absorption in excess of 900 nm.

BRIEF DESCRIPTION OF THE DRAWINGS

The invention will now be described in more detail with reference to FIGURE, in which:

FIG. 1 is a schematic view of a measuring device for optically determining a concentration of alcohol and carbohydrates in a liquid sample according to one embodiment of the invention.

DETAILED DESCRIPTION OF THE INVENTION

In view of the FIGURE, the device will now be described more fully hereinafter. In FIG. 1 a measuring device for measuring a concentration of alcohol and carbohydrates in a liquid sample 3 is shown in which light is used for determining the respective concentrations. The device includes a reflecting surface 1, which has the advantage that the light provided by the light sources 7, 10 is reflected via said reflecting surface and directed to the entrance of the spectrometer 11. Thus, all the elements, with the exception of the reflecting surface 1, are included in one housing 12.

The illustrated embodiment includes two light sources 7, 10. More light sources may be used in another embodiment. The light sources 7, 10 are in particular Light Emitting Diodes, LEDs, as LEDs have the advantage that they are better suited for producing light of a particular wavelength or wavelength range, that they consume less energy and that they are capable of providing a more suitable light beam in comparison with, for example, gas discharge lamps. Various shapes and configurations of LEDs can be used, as long as they are arranged to provide light at least in the range between 750 nm and 1000 nm; the LEDs may be non-monochromatic LEDs, monochromatic LEDs or a multitude of monochromatic LEDs with different wavelengths.

Since the LEDs already provide slightly beamed light, the device can in principle also operate without directing elements. In a preferred embodiment, however, the device includes directing elements. Examples of such directing elements may include, for example, parabolic reflectors as indicated by reference numerals 6 and 9, or other mirrors or lenses. The light from the LEDs can be directed in such a manner by means of said directing elements that a parallel light beam is provided. In one embodiment they may also function as diffraction elements for thus separating light comprising several wavelengths or non-monochromatic light into two different wavelengths and causing said light to shine in separate directions. The LEDs may be provided with active cooling means which, through the use of a temperature sensor 16, 17, ensure that a constant temperature of the LED elements is maintained. Said active cooling means are preferably configured as a Peltier element 15, 18.

FIG. 1 in particular shows two polarization filters 5, 8. Due to the presence of said polarization filters, the device can be provided with one spectrometer in a relatively simple manner, while no additional elements are needed for causing light to shine alternately (either in the time domain or in the frequency domain) on the spectrometer. The lenses enable the spectrometer to distinguish between light from the first light source and light from the second light source.

By means of the spectrometer 11, the light intensity of the incident light is plotted against a wavelength. In this way it can be determined at which wavelength the light intensity is higher or lower. The control unit 13, in the form of electronics, a microprocessor or other arithmetic unit, which is connected to the spectrometer can plot the absorption of the light against the wavelength by comparing it with a reference value. Preceding that, a so-called dark measurement is carried out, wherein the electronic noise in the spectrum is measured in the dark at the set temperature, without the LEDs emitting light.

The exemplary embodiment of the measuring device as shown in FIG. 1 further includes a temperature sensor 14. By means of said sensor the temperature of the liquid sample present in the measuring chamber (product line) 2 can be determined. If said temperature falls outside a predetermined measuring range, this must at least be taken into account in the presentation by the device of the respective concentrations of alcohol and carbohydrates. The device provides the most accurate concentration determinations at a calibrated sample temperature.

The liquid sample, being beer, wine, liquors or another one of the aforesaid beverages, can be statically sampled. In an alternative preferred embodiment, however, the liquid sample can also be passed through the measuring chamber, in this case in the form of the product line 2 shown in FIG. 1. The device is suitable for both embodiments, with the latter rendering the device suitable in particular for being incorporated in a production line.

Various modifications, additions an alternative can be realised by the skilled person on the basis of the above description, which modifications, additions an alternative all fall within the scope of the appended claims.

What is claimed is:

1. A device installed in a production line for optically determining a concentration of alcohol and carbohydrates in a liquid sample, comprising:
   a first and a second light source arranged for exposing and emitting light through the liquid sample having a wavelength ranging between 750 nm and 1000 nm from the first and second light source as the liquid sample is passing through a measuring chamber in the production line;
   a spectrometer arranged to determine a first and a second light intensity by measuring the light from the first and the second light source emitted through the liquid sample;
   a temperature sensor for measuring a temperature of said liquid sample in the production line;
   a processing unit connected to the spectrometer and arranged to determine an absorption value of the liquid sample from a comparison of the first and the second light intensity with a reference value and
   two polarization filters for filtering the light from the first light source, wherein:
   the processing unit is further arranged to calculate and present the concentration of alcohol from the proportion of the absorption at a wavelength of less than 900 nm and the wavelength range between 900 nm and 920 nm, and to calculate and present the concentration of carbohydrates from the proportion of the absorption in the wavelength range between 750 nm and 900 nm and at a wavelength of 900 nm, wherein the processing unit is arranged to determine if the measured temperature in the production line is outside of a predetermined range, and wherein an outcome thereof defines reliability of the calculated concentrations; and
   the first polarization filter is positioned between the first light source and the liquid sample and the second polarization is positioned between the liquid sample and the spectrometer, and wherein the liquid sample is selected from the group consisting of beer, wine, liquors, low-alcohol beer, non-alcoholic beer, and soft drinks.

2. The device of claim 1, wherein the first and second polarization filters are positioned at an angle relative to each other, the angle ranging from 10 to 170 degrees.

3. The device of claim 1, wherein the processing unit is arranged to formulate a linear equation from a plurality of reference measurements and to calculate the concentrations of carbohydrates and alcohol from the linear equation.

4. The device of claim 3, wherein the linear equation is a simple linear regression or multiple linear regression analysis.

5. The device of claim 1, further comprising a reflecting surface for reflecting the light from the first and the second light source to the spectrometer.

6. The device of claim 1, further comprising a first and a second lens element for focusing the light from the first and the second light source to the spectrometer.

7. The device of claim 1, further comprising a window for closing the device to the liquid sample, and
   the window is arranged to only transmit light in the wavelength range between 750 nm and 1000 nm.

8. The device of claim 1, further comprising temperature control means for maintaining the liquid sample at a constant, predetermined temperature.

9. The device of claim 1, wherein the spectrometer comprises a monochromator.

10. The device of claim 1, wherein the alcohol comprises ethanol.

11. The device of claim 10, wherein the carbohydrates consist of an extract comprising at least one or more from the group of glucose, maltose, dextrine, fructose, and sucrose.

12. A method for optically determining a concentration of alcohol and carbohydrates in a liquid sample by a device installed in a production line, comprising the steps of:
   providing the liquid sample and passing the liquid sample through a measuring chamber of the device installed in the production line;
   exposing the liquid sample to a first and a second light source in which the light sources are arranged to alternately expose the liquid sample to a wavelength ranging between 750 nm and 1000 nm by emitting light from the first and second light sources through the liquid sample as the liquid sample is passing through the measuring chamber of the device installed in the production line;
   determining a first and a second light intensity by means of a spectrometer by measuring the light emitted through the liquid sample from the first and the second light sources;
   measuring temperature of said liquid sample in the production line with a temperature sensor;
   determining with a processing unit, an absorption value of the liquid sample by comparing the first and the second light intensity with a reference value;
   calculating and presenting with a processing unit, the concentration of alcohol from the proportion of the absorption in the wavelength range of less than the 900 nm and the wavelength range between 900 nm and 920 nm and
   the concentration of carbohydrates from the proportion of the absorption between 750 nm and 900 nm and the absorption in excess of 900 nm, wherein:
   the liquid sample is selected from the group consisting of beer, wine, liquors, low-alcohol beer, non-alcoholic beer, and soft drinks, wherein:
   the processing unit is arranged to determine if the measured temperature in the production line is outside of a predetermined range, and wherein an outcome thereof defines reliability of the calculated concentrations.

13. The method for optically determining a concentration of alcohol and carbohydrates in a liquid sample according to claim 12, further comprising
- defining a linear equation from a plurality of reference measurements; and
- calculating the concentration of carbohydrates and alcohol from the linear equation, wherein:
- the linear equation is a simple or multiple linear regression analysis.

* * * * *